(12) United States Patent
Guillon et al.

(10) Patent No.: US 8,167,427 B2
(45) Date of Patent: May 1, 2012

(54) MULTIFOCAL CONTACT LENSES MANUFACTURED FROM A RESPONSIVE POLYMER GEL

(76) Inventors: Michel Guillon, London (GB); Cecile Adrienne Maissa, London (GB)

( * ) Notice: Subject to any disclaimer, the term of this patent is extended or adjusted under 35 U.S.C. 154(b) by 533 days.

(21) Appl. No.: 10/596,640

(22) PCT Filed: Dec. 20, 2004

(86) PCT No.: PCT/GB2004/005350
§ 371 (c)(1),
(2), (4) Date: Nov. 15, 2006

(87) PCT Pub. No.: WO2005/059632
PCT Pub. Date: Jun. 30, 2005

(65) Prior Publication Data
US 2007/0091260 A1  Apr. 26, 2007

(30) Foreign Application Priority Data
Dec. 19, 2003 (GB) ................................. 0329507.8

(51) Int. Cl.
*G02C 7/04* (2006.01)
(52) U.S. Cl. .................................. 351/160 H; 351/161
(58) Field of Classification Search .............. 351/160 R, 351/160 H, 161, 177
See application file for complete search history.

(56) References Cited

U.S. PATENT DOCUMENTS

| | | | |
|---|---|---|---|
| 2,976,576 A * | 3/1961 | Wichterle et al. ............... 264/49 |
| 4,188,373 A | 2/1980 | Krezanoski | |
| 5,108,169 A * | 4/1992 | Mandell ........................ 351/161 |
| 5,252,318 A | 10/1993 | Joshi | |
| 5,448,312 A | 9/1995 | Roffman | |
| 5,485,228 A | 1/1996 | Roffman | |
| 5,503,893 A | 4/1996 | Evans | |
| 5,712,721 A * | 1/1998 | Large ........................... 359/245 |
| 5,835,192 A | 11/1998 | Roffman | |
| 5,840,338 A * | 11/1998 | Roos et al. ..................... 424/488 |
| 6,179,420 B1 | 1/2001 | Roffman | |
| 6,364,482 B1 | 4/2002 | Roffman | |
| 6,511,178 B1 | 1/2003 | Roffman | |
| 7,264,351 B2 * | 9/2007 | Shadduck ...................... 351/159 |
| 7,278,739 B2 * | 10/2007 | Shadduck ...................... 351/177 |
| 7,423,801 B2 * | 9/2008 | Kaufman et al. ............. 359/319 |

FOREIGN PATENT DOCUMENTS

| | | |
|---|---|---|
| WO | 9524430 | 9/1995 |
| WO | 9700275 | 1/1997 |

OTHER PUBLICATIONS

Hu, Z., et al, "Synthesis and Application of Modulated Polymer Gels", Science, 1995, vol. 269, pp. 525-527.
Kataoka, K., et al, "Totally Synthetic Polymer Gels Responding to External Glucose Concentration: Their Preparation and Application to On-Off Regulation of Insulin Release", J. Am. Chem. Soc., 1998, 120, (48), pp. 12694-12695.
Kurauchi, T., et al, "Deformation Behaviors of Polymer Gels in Electric Field", Polymer Gels, D. DeRossi, et al, Eds., 1991, pp. 237-247, Plenum Press, New York.
Li, Y., et al, "Shape Memory Gels Made by the Modulated Gel Technology", J. Appl. Poly. Sci., 1997, 63, pp. 1173-1178.
Osada, Y. & Ross-Murphy, S.B., "Intelligent Gels", Scientific American, May 1993, pp. 42-47.
Ruben, M. & Guillon, M., Presbyopia and the Influence of Aging on Prescription of Contact Lenses (W.J. Benjamin, I.M. Borish), Contact Lens Practice, 1994, Chapter 33 (pp. 763-825), Chapman & Hall, London.
Tanaka, T., et al, "Collapse of Gels in an Electric Field", Science, 1982, vol. 218, pp. 467-469.
Tanaka, T., et al, "Polymer Gels That Can Recognize and Recover Molecules", Faraday Discussions, 1996, 102, pp. 201-206.

* cited by examiner

*Primary Examiner* — Scott J Sugarman
(74) *Attorney, Agent, or Firm* — Senniger Powers LLP

(57) ABSTRACT

A multi-focal contact lens wherein the lens is manufactured at least partially from a responsive polymer gel.

11 Claims, 2 Drawing Sheets

MULTIFOCAL CONTACT LENSES MANUFACTURED FROM A RESPONSIVE POLYMER GEL

The present invention relates to lenses such as contact lenses, intra-ocular lenses, implant lenses, inlay lenses, onlay lenses or any other ophthalmic refracture devices. For ease of reference these lenses will be referred to collectively as "contact lenses". Thus any reference to "contact lenses", "contact lens", "lenses", "lens" and the like will be understood to include at least the above-mentioned lenses.

In one arrangement, the present invention relates to bifocal or multi-focal contact lenses formed from so-called intelligent polymers.

As the popularity of contact lenses has increased over the use of glasses to correct vision, it has become desirable to address the problems encountered by users who require correction of their vision for both near and distance viewing. It is therefore desirable to develop bifocal, and preferably multi-focal, contact lenses.

Examples of arrangements of bifocal contact lenses are known. One arrangement known as Alternating Image bifocals or Alternating Vision bifocals has a distance viewing region located in the upper portion of the lens and a near-viewing portion located in the bottom portion of the lens. The two parts of the lens are separated by a line extending across the lens that may be straight or curved. A review of typical designs for these lenses can be found in Ruben M. & Guillon M. (1994), Chapter 33 Presbyopia and Influence of Aging on Prescription of Contact Lenses (W J Benjamin, I M Borish) Chapman & Hall, London, UK.

These bifocal contact lenses function by taking a different position in straight ahead gaze and in down gaze. Theoretically, in straight ahead gaze the pupil is covered by the distance zone and in down gaze the contact lens is higher and the pupil is covered by the near zone. However, this arrangement suffers from certain disadvantages.

One disadvantage of this arrangement is that it is difficult to precisely control the movement of the lens so that the pupil is alternately covered by the near and distance position. To achieve this is a skillful process that is time-consuming and not always successful. Failure to achieve optimal pupil coverage has the disadvantage that the user looks through both the distance and near positions simultaneously resulting at times in two images at once which is known as "ghosting" and habitually in a decrease in visual acuity compared that achieved with spectacles.

A second disadvantage is that for an Alternating Vision bifocal to perform optically it is required to move significantly more than is optimum for comfort and thus the user may experience some discomfort. Further it may be necessary to provide features on the lens to control its rotation. However, these features may increase the thickness and the irregularity of the contact lens which may result in lower comfort than the conventional simple design.

A still further disadvantage of this arrangement is that the separation line provides a discontinuity on the surface of the contact lens. If the line is situated on the anterior surface of the contact lens it can catch the eyelid, create discomfort, and pull the lens out of position at least temporarily impairing the user's vision. If the separation line is placed on the back surface of the lens it may create mechanical trauma to the ocular tissue.

An alternative lens arrangement is known under the generic term of Simultaneous Image bifocal or multifocal. These contact lenses are typically formed from two or more concentric zones of alternating distance and near power or a single zone of continuously changing power (progressive). Two options are available. In the first a centre near contact lens is known in which the near power is at the centre of the lens. In the second, a centre distance contact lens with the opposite arrangement is known. Typically for the progressive design the near portion will be in the centre but the opposite arrangement is known. Concentric zones design are commonly available both in centre near or centre distance designs. (Ruben M. & Guillon M. (1994), Chapter 33 Presbyopia and Influence of Aging on Prescription of Contact Lenses (W J Benjamin, I M Borish) Chapman & Hall, London, UK.).

One benefit of these lenses is that they do not require movement to perform as bifocals. However, they do require excellent centration during both distance and near gaze. This requirement is a disadvantage compared to single vision contact lenses in making fitting more exacting. The principal disadvantage of these designs is due to the fact that in order to function they focus a distance and near image on the retina at all times.

A further disadvantage is that they produce a retinal image of poorer quality than that obtained with single vision contact lenses or spectacles. For example, during distance gaze only part of the pupil is covered by the distance optics which form the in focus image, the rest of the pupil is covered by out of focus intermediate and/or near zones which degrade the quality of the image produced on the retina and consequently decrease visual performance.

A still further disadvantage is that the size of pupils varies between patients and more importantly for each patient with different levels of luminance. This has the drawback that the exact percentage of light forming the distance and near images are not controlled. Various suggestions have been made to address this through the use of "pupil intelligent" arrangements and/or the use of "binocular pair" where one contact lens favours near and one favours distance vision. For example, one lens may have a centre near design and the other a centre distance design. However, even with these modifications, the above-mentioned drawbacks remain.

In a further alternative arrangement it has been proposed to use two materials of different refractive indexes to produce either Alternating Vision or Simultaneous Vision bifocal or multifocal lenses. However these differing manufacturing processes do not overcome the mechanical problems of the former and the visual problems of the latter.

In other alternative arrangements Simultaneous Vision bifocal lenses are produced utilising diffractive rather than refractive principles. The disadvantage of the compromised vision is similar in both cases and in addition a significant amount of light is lost making vision at night even more problematic than with refractive contact lenses.

Examples of prior art contact lenses can be found in U.S. Pat. No. 6,511,178, U.S. Pat. No. 6,364,482, U.S. Pat. No. 5,835,192, U.S. Pat. No. 6,179,420, U.S. Pat. No. 5,835,192, U.S. Pat. No. 5,485,228 and U.S. Pat. No. 5,448,312.

It is therefore desirable to provide bi- or multi-focal contact lenses which overcome the above-mentioned drawbacks and disadvantages. For ease of reference bi- and multi-focal contact lenses will, for the purposes of this application, be collectively referred to as multi-focal lenses.

In addition it is desirable to provide a multi-focal contact lens which offers other advantages such as one or more of: providing the quality of vision that is achievable with conventional single vision contact lenses for both distance and near vision; be of a quality of vision similar to that achievable with single vision contact lenses for any intermediate viewing distances; does not require significant contact lens movement when the direction of gaze goes from distance to near and vice versa for the user to achieve the expected visual performance; and are as easily fitted as conventional single vision lenses.

A contact lens having some or all of these desirable attributes can be obtained by the use of a responsive polymer gel. These responsive polymers are also known as "smart polymers" or "intelligent polymers".

DETAILED DESCRIPTION

Thus according to the present invention there is provided a multi-focal contact lens wherein the lens is manufactured at least partially from a responsive polymer gel.

Responsive polymers have been known for some time and are polymeric materials which have the capacity to respond to external stimuli such as temperature, pH, ionic strength, light, electric field, magnetic field, shear forces or a chemical trigger. The responsive polymers are generally polymer networks. These networks are polymer-polymer compositions where there are favorable interactions between the constituent polymers. The interaction may be covalent bonding, coulombic attraction, hydrogen bonding, Van der Waals attractions, and physical interactions such as entanglement. Examples of responsive polymers can be found in U.S. Pat. No. 5,503,893, WO 97/00275, U.S. Pat. No. 4,188,373, U.S. Pat. No. 5,252,318, WO 95/24430, Katoaka K et al. Journal of the American Chemical Society. December 1998, Tanaka T et al Faraday Discuss, 101, 201 (1995), Li Y, Hu Z, Chen Y. "Shape memory gels made by the modulated gel technology, J Appl Poly Sci 63: 1173-1178 (1997), Hu Z. Science 269:525 (1995), Tanaka et al Collapse of gels in an electric field Science 218:457-469 (1982), Osada Y, Ross-Murphy SB. Intelligent gels Scientific American, May 1993 pp 42 and Karauchi T et al "Deformation behaviors of polymer gels in electric field" In Polymer Gels. Ed. D. DeRossi et al Plenum Press, NY, 1991, pp 237 which are incorporated herein by reference.

Any suitable responsive polymer gel may be used in the present invention. The polymer gel is preferably compatible with ocular tissue. If the polymer gel is not compatible with ocular tissue, it may be included within the contact lens to avoid direct interaction between the polymer and the ocular tissue. Particularly preferred are those which will change shape and/or refractive index under changes in environmental conditions and/or when a stimulus such as an electric or magnetic field is applied.

The stimulus for changing the shape of the lens can be provided by the ocular environment around the contact lens or alternatively by any artificial means within the contact lens.

The device may include a detector and separately a device for causing the stimulus.

In one arrangement, a device embedded in one or both contact lens will produce localised changes that will trigger the responsive polymer to reversibly modify its shape.

In one arrangement of the present invention, the contact lens will change shape with the change in stimulus. This change in the shape will alter the focus distance of the lens.

Figure 2:
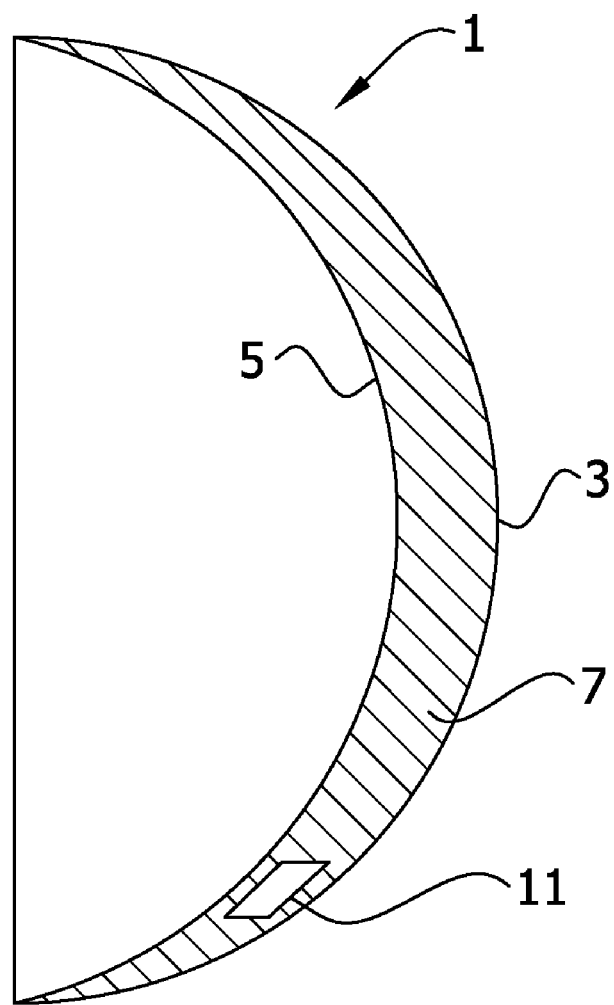
FIG. 2 is a section taken in the plane 2-2 of FIG. 1.

The change in shape of the contact lens can be localised to the front surface 3 and/or back surface 5 and/or an embedded zone 7 within the contact lens, as best illustrated in FIG. 2.

In one alternative arrangement the responsive polymer will only comprise the optical zone and/or will be embedded in the anterior or posterior of the contact lens.

It will be acknowledged that the present invention will enable the user to focus at any desired distance without the problems associated with the lenses of the prior art. In particular there is no requirement for movement of controlled amplitude during change of gaze. In addition, at each distance of gaze, viewing is through the entire lens and so the disadvantages of optical distortions and/or complicated head movements noted in the prior art arrangements are obviated.

A further advantage of the present invention is that the lenses can be more readily fitted than the prior art lenses since they will neither require a complex mechanical fit or the adjustment of the optical power of the contact lens from the best sphere spectacle correction and near addition other than the compensation for back vertex distance.

Figure 1:
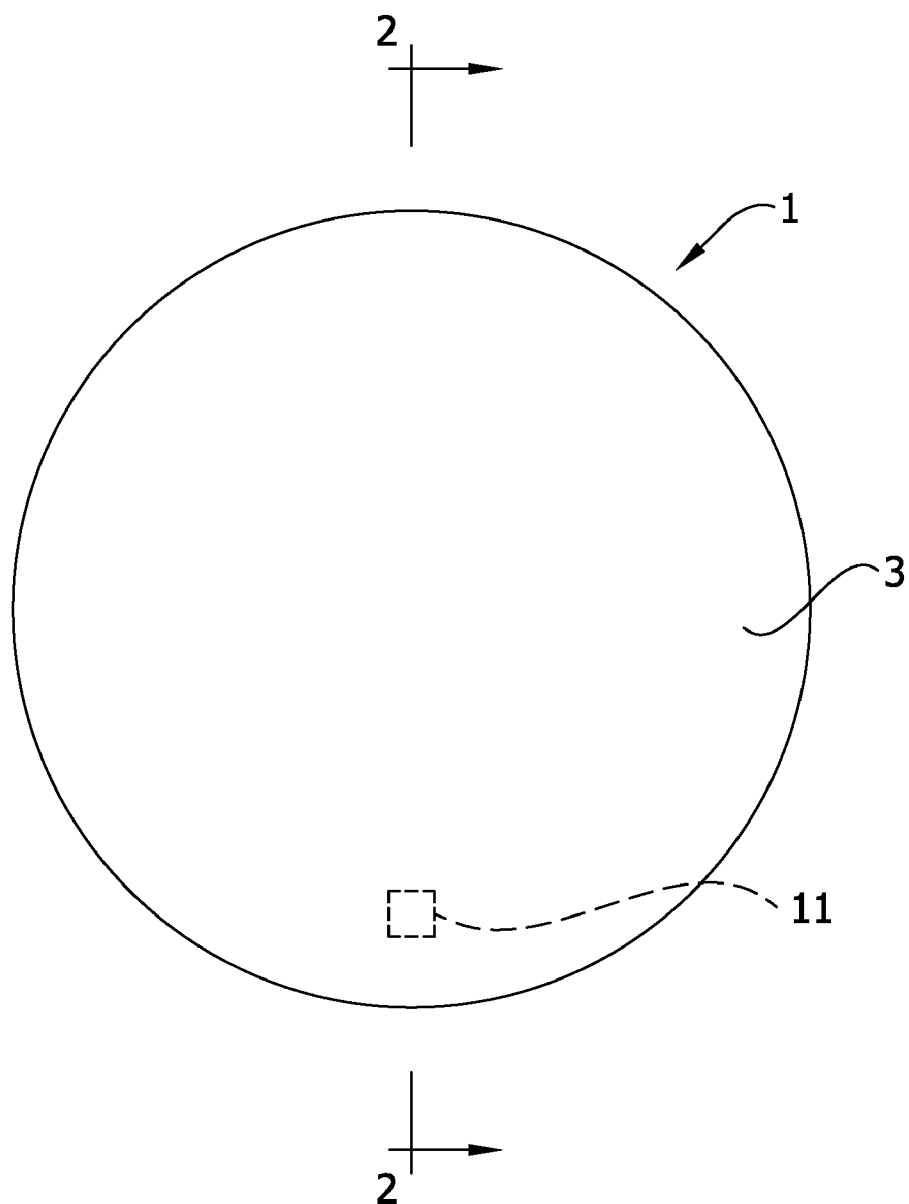
FIG. 1 is a front view of a contact lens of the invention.

The stimulus for changing the shape of the contact lens surfaces or the shape of an embedded part of the lens may be provided by an electric field produced by means imbedded in the contact lens itself. Any suitable means for providing the electric field may be used. In one arrangement, illustrated in FIGS. 1-2, a chip 11 may be embedded in the contact lens 1. The chip 11 may be a nano or micro chip and will generally be configured to that it is not visible to the user. The chip may be triggered to emit the electric field by any suitable means.

The stimulus for changing the shape of the contact lens surfaces or the shape of an embedded part of the lens may be provided by a magnetic field produced by means imbedded in the contact lens itself. Any suitable means for providing the magnetic field may be used. In one arrangement a chip may be embedded in the contact lens. The chip may be a nano or micro chip and will generally be configured so that it is not visible to the user. The chip may be triggered to emit the magnetic field by any suitable means.

In one arrangement, the chip will monitor the eye movement and a change in eye movement will cause the chip to emit the field required to cause the responsive polymer to change shape. The monitoring of the eye movement may be carried out by the chip itself or by a separate detector in communication with the chip.

For example, the chip may be triggered when the user gazes inwardly and the lens may alter shape such that the user is able to clearly focus on close material.

In one alternative arrangement, the chip or a separate detector may identify the inter-pupillary distance which is the distance between the pupils of the right and left eye. When the user is looking straight ahead, the distance between the two eyes is at its maximum. In one arrangement, it would be desirable to arrange that the chip does not issue any field in this circumstance or it may issue a maximum or minimum field. As the user looks at a point that is closer to the user, the pupils of the eyes move closer together and this will be detected. The chip will react to the change in distance and will modulate the field present to cause the shape of the responsive polymer to change such that focusing can be achieved. As the user looks at still closer points the eyes come closer together, the current produced by the chip will change in intensity to give a proportional change in the contact lens front surface which will alter the power of the lens. As the user looks away again, the field will change in intensity and the shape of the lens will revert to that required for distance vision.

In a second alternative arrangement the chip will monitor the relative distance of a pair of contact lenses. When the user passes from distance gaze to near distance gaze, the contact lenses move with the eye and get closer together. The change in relative distance between the two contact lenses will produce a change in the power.

Thus in a most preferred arrangement, the lens will provide an exact correction for all focusing distances. This is particularly possible with responsive polymers which have a reaction time that is sufficiently fast that the change is not noticeable by the user so they experience clear vision.

In an alternative preferred arrangement, the lens will provide a correction for the focusing distance once a set threshold or a series of set threshold in stimulus have been reached.

Additionally or alternatively to the current resulting in a change in shape, the field may induce a change in refractive index.

Whilst the foregoing has been specifically described with reference to a chip producing an electrical field, it will be acknowledged that other means for producing a suitable stimulus may be used.

The invention claimed is:

1. A multi-focal contact lens wherein the lens is manufactured at least partially from a responsive polymer gel capable of changes in shape when worn by a wearer of the contact lens, wherein the responsive polymer gel responds to the application of stimulus corresponding to a detected condition in at least one eye of the wearer.

2. A multi-focal contact lens according to claim 1 wherein the responsive polymer gel changes shape and/or refractive index.

3. A multi-focal contact lens according to claim 1 wherein the stimulus is an electric field.

4. A multi-focal contact lens according to claim 1 wherein the stimulus is a magnetic field.

5. A multi-focal contact lens according to claim 1 wherein the stimulus is produced by means embedded in the contact lens itself.

6. A multi-focal contact lens according to claim 5 wherein the means of providing the stimulus is a nano or micro chip.

7. A multi-focal contact lens wherein:
the lens is manufactured at least partially from a responsive polymer gel that responds to application of stimulus produced by a nano or micro chip embedded in the contact lens itself; and
the chip monitors eye movement such that a change in eye movement causes the chip to emit the stimulus.

8. A multi-focal contact lens wherein:
the lens is manufactured at least partially from a responsive polymer gel that responds to application of stimulus produced by a nano or micro chip embedded in the contact lens itself; and
the chip monitors inter-pupillary distance and emits the stimulus when inter-pupillary distance changes.

9. A multi-focal contact lens wherein:
the lens is manufactured at least partially from a responsive polymer gel that responds to application of stimulus produced by a nano or micro chip embedded in the contact lens itself; and
the chip monitors a distance between right and left contact lenses and emits the stimulus when the distance changes.

10. A multi-focal contact lens wherein the lens is manufactured at least partially from a responsive polymer gel, said lens capable of changes in shape with stimulus during use by a wearer of the lens, wherein said at least one stimulus is responsive to eye movement of the wearer of the lens, and wherein said at least one stimulus is selected from the group consisting of temperature, pH, ionic strength, light, electric field, magnetic field, shear forces, and a chemical trigger.

11. A multi-focal contact lens wherein the lens is manufactured at least partially from a responsive polymer gel capable of changing shape when worn by a wearer of the lens, said changing shape triggered by eye movement of the wearer of the lens.

* * * * *